United States Patent
Yu et al.

(10) Patent No.: US 7,348,471 B2
(45) Date of Patent: Mar. 25, 2008

(54) RICE GLUTELIN GENE PROMOTERS

(75) Inventors: Su-May Yu, Taipei (TW); Chwan-Yang Hong, Yun-Lin County (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 10/819,371

(22) Filed: Apr. 5, 2004

(65) Prior Publication Data

US 2005/0066387 A1   Mar. 24, 2005

Related U.S. Application Data

(60) Provisional application No. 60/460,037, filed on Apr. 3, 2003.

(51) Int. Cl.
*A01H 1/00* (2006.01)
*C07H 21/04* (2006.01)
*C12N 15/00* (2006.01)

(52) U.S. Cl. .................. 800/287; 435/6; 435/69.1; 435/468; 435/419; 435/320.1; 536/24.1; 800/295

(58) Field of Classification Search .............. 800/295; 435/320.1; 536/23.1
See application file for complete search history.

(56) References Cited

FOREIGN PATENT DOCUMENTS

JP   11/332584   12/1999
WO   98/42853   10/1998

OTHER PUBLICATIONS

Rodriguez et al. Accession No. AAV61593. Date: Dec. 17, 1998. Database: Geneseq.*
Yoshimi et al. Accession No. E64476. Date: Jun. 18, 2001. Database: GenBank.*
Patel et al. Mol Breeding. 2000, vol. 6, pp. 113-123.*
Wu et al. (2000), Quantitative nature of the Prolamin-box, ACGT and AACA motifs in a rice glutelin gene promoter: minimal cis-element requirements for endosperm-specific gene expression. Plant J. Aug. 2000;23(3):415-21.
Wu et al. (1998), The GCN4 motif in a rice glutelin gene is essential for endosperm-specific gene expression and is activated by Opaque-2 in transgenic rice plants. Plant J. Jun. 1998;14(6):673-83.
Wu et al. (1998) Promoters of Rice Seed Storage Protein Genes Direct Endosperm-Specific Gene Expression in Transgenic Rice, Plant Cell Physiology, vol. 39, No. 8, pp. 885-889, 1998.
Qu et al. (2004) Evaluation of Tissue Specificity and Expression Strength of Rice Seed Component Gene Promoters in Transgenic Rice, Plant Biotechnology Journal, vol. 2, pp. 113-125, 2004.
Takaiwa et al. (1996) Characterization of Common cis-Regulatory Elements Responsible for the Endosperm-Specific Expression of Members of the Rice Glutelin Multigene Family, Plant Molecular Biology, vol. 30, pp. 1207-1221, 1996.
Yoshihara et al. (1996) A 45-bp proximal Region Containing AACA and GCN4 Motif is Sufficient to Confer Endosperm-Specific Expression of the Rice Storage Protein Glutelin Gene, GLuA-3, FEBS Letters, vol. 383, pp. 213-218, 1996.
Yoshihara et al. (1996) Cis-regulatory elements responsible for quantitative regulation of the rice seed storage protein glutelin *GluA-3* gene. Plant Cell Physiol 37:107-111, 1996.

* cited by examiner

*Primary Examiner*—Phuong T Bui
(74) *Attorney, Agent, or Firm*—Occhiuti Rohlicek & Tsao LLP

(57) ABSTRACT

A nucleic acid containing a glutelin gene promoter. Disclosed are transformed plant cells and transgenic plants containing a nucleic acid that includes the promoter operably linked to a sequence encoding heterologous protein. Also disclosed are methods of making the transformed plant cells and transgenic plants and methods for expressing a polypeptide.

22 Claims, No Drawings

RICE GLUTELIN GENE PROMOTERS

RELATED APPLICATION

This application claims priority to U.S. application Ser. No. 60/460,037, filed Apr. 3, 2003, the contents of which are incorporated herein by reference.

BACKGROUND

Transgenic plants and transformed plant cells have been used for producing recombinant proteins, such as enzymes, antibodies, vaccines, and therapeutic proteins. See, e.g., Fischer et al., 2000, Transgenic Res. 9: 279-299; Giddings et al., 2000, Nat. Biotechnol. 18: 1151-1155; Stoger et al., 2002, Curr. Opin. Biotechnol. 13: 161-166; and Ma et al., 2003, Nat. Rev. Genet. 4: 794-805. The plant-based expression systems offer several advantages over others. For example, they (1) have very little risk of contamination with mammalian pathogens or bacterial toxins, (2) are capable of protein post-translation modification, (3) are more economic than bioreactor-based systems, (4) can be scaled up at relatively low costs, (5) can be developed within a short timeframe, and (6) require no or partial purification if the recombinant proteins are used directly as foods, feed supplements, or raw materials for use. In particular, since plant cells are able to properly process recombinant mammalian proteins, these systems have been used to produce functional and complex mammalian proteins (Sijmons et al., 1990, Biotechnology 8: 217-221; Hiatt et al., Nature 342: 76-78 and During et al., Plant Mol. Biol. 15: 281-293). Nonetheless, they also have limitations. In many cases, the amount of expressed protein ranges from 0.001% to 0.1% of total soluble proteins (Daniell et al., 2001, Trends Plant Sci. 6: 219-226), which is too low for commercial production. Thus, there is a need for a high yield plant expression system.

SUMMARY

This invention is based on the discovery that novel rice glutelin B gene promoters (GluB-1 promoters) drive high level expression of a heterologous recombinant protein in a plant cell. An exemplary GluB-1 promoter (SEQ ID NO: 2) is shown below. It corresponds to nucleotides (nt) −1307 to +36 of the rice glutelin B gene (GluB), where position +1 represents the transcription start site of the gene.

```
-1307 gatctcgatt tttgaggaat tttagaagtt gaacagagtc aatcgaacag acagttgaag  (SEQ ID NO: 2)

-1247 agatatggat tttctaagat taattgattc tctgtctaaa gaaaaaaagt attattgaat

-1187 taaatggaaa aagaaaaagg aaaaagggga tggcttctgc tttttgggct gaaggcggcg

-1127 tgtggccagc gtgctgcgtg cggacagcga gcgaacacac gacggagcag ctacgacgaa

-1067 cgggggaccg agtggaccgg acgaggatgt ggcctaggac gagtgcacaa ggctagtgga

-1007 ctcggtcccc gcgcggtatc ccgagtggtc cactgtctgc aaacacgatt cacatagagc

-947 gggcagacgc gggagccgtc ctaggtgcac cggaagcaaa tccgtcgcct gggtggattt

-887 gagtgacacg gcccacgtgt agcctcacag ctctccgtgg tcagatgtgt aaaattatca

-827 taatatgtgt ttttcaaata gttaaataat atatataggc aagttatatg ggtcaataag

-767 cagtaaaaag gcttatgaca tggtaaaatt acttacacca atatgcctta ctgtctgata

-707 tattttacat gacaacaaag ttacaagtac gtcatttaaa aatacaagtt acttatcaat

-647 tgtagtgtat caagtaaatg acaacaaacc tacaaatttg ctattttgaa ggaacactta

-587 aaaaaatcaa taggcaagtt atatagtcaa taaactgcaa gaaggcttat gacatggaaa

-527 aattacatac accaatatgc tttattgtcc ggtatatttt acaagacaac aaagttataa

-467 gtatgtcatt taaaaataca agttacttat caattgtcaa gtaaatgaaa acaaacctac

-407 aaatttgtta ttttgaagga cacctaaat tatcaaatat agcttgctac gcaaaatgac

-347 aacatgctta caagttatta tcatcttaaa gttagactca tcttctcaag cataagagct

-287 ttatggtgca aaaacaaata taatgacaag gcaaagatac atacatatta agagtatgga

-227 cagacatttc tttaacaaac tccatttgta ttactccaaa agcaccagaa gtttgtcatg

-167 gctgagtcat gaaatgtata gttcaatctt gcaaagttgc ctttccttt gtactgtgtt

-107 ttaacactac aagccatata ttgtctgtac gtgcaacaaa ctatatcacc atgtatccca

-47 agatgctttt ttattgctat ataaactagc ttggtctgtc tttgaactca catcaattag

+14 cttaagtttc cataagcaag tac
```

Accordingly, the invention features a nucleic acid containing a GluB-1 promoter. A GluB-1 promoter as used herein refers to two types of nucleic acids.

The first type GluB-1 promoter is an isolated nucleic acid sequence that (1) contains SEQ ID NO: 1 (corresponding to nt −1307 to −1 of the sequence list above) or its complement, and (2) is 1,307 to 2,300 (i.e., any integer between 1,307 and 2,300, inclusive) nucleotides in length. An "isolated nucleic acid" is a nucleic acid the structure of which is not identical to that of any naturally occurring nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by PCR amplification, or a restriction fragment; and (d) a recombinant nucleotide sequence, e.g., a nucleotide sequence containing heterologous sequences or encoding a fusion protein.

The second type GluB-1 promoter is a nucleic acid sequence that (1) contains tatccatatcca (SEQ ID NO: 9) or cctacgtggc (SEQ ID NO: 14), or its complement, and (2) is at least 20 (i.e., any integer no less than 20, e.g., 40, 60, 100, 500, 1,000, or 2,000) nucleotides in length. SEQ ID NOs: 9 and 14 are mutant forms of SEQ ID NO: 2 regions from nt −54 to −43 (SEQ ID NO: 8) and from nt −82 to −73 (SEQ ID NO: 13), respectively. Shown below is the nt −92 to −28 region of SEQ ID NO: 2. This region, i.e., SEQ ID NO: 3, spans SEQ ID NOs: 8 and 13 (both underlined).

the invention features a vector containing a promoter that includes one of the above described nucleic acids. The promoter can be further operatively linked to a recombinant nucleic acid that encodes a heterologous protein of interest.

The invention further features a transformed plant cell that contains (1) the above described promoter sequence and (2) a recombinant nucleic acid that encodes a heterologous protein and is operatively linked to the promoter sequence. In one embodiment, the plant cell is a monocot plant cell, such as a cereal plant cell (e.g., a rice cell, a corn cell, a wheat cell, a barley cell, an oat cell, or a sorghum cell). In another embodiment, the plant cell is a dicot plant cell, e.g., a tobacco cell, a potato cell, a tomato cell, or a soybean cell. To make the plant cell described above, one can introduce into a plant cell the promoter sequence and the recombinant nucleic acid. In one embodiment, the transformed plant cell is a cultured cell. Exemplary cultured cells include protoplasts, calli, suspension cells, and tissues.

The invention also features a transgenic plant whose genome contains (1) one of the above-described promoter sequences and (2) a recombinant nucleic acid that encodes a heterologous protein and is operatively linked to the promoter sequence. The plant can be (1) a monocot plant, including a cereal plant, e.g., rice, corn, wheat, barley cell, oat, or sorghum; or (2) a dicot plant, e.g., tobacco, potato, tomato, or soybean. To make such a transgenic plant, one

```
SEQ ID NO: 3:
             -82      -73                     -57 -54         -43  -39
              |        |                       |   |           |    |
-92atatattgtctgtacgtgcaacaaactatatcaccatgtatcccaagatgcttttttattgctat-28
            SEQ ID NO: 13                   SEQ ID NO: 8
```

In one mutant, the region corresponding to nt −57 to −39 of SEQ ID NO: 3 is atgTATCCATATCCActtt (SEQ ID NO: 10) or cctTATCCATATCCAcgcc (SEQ ID NO: 11). Both SEQ ID NOs: 10 and 11 include SEQ ID NO: 9 (shown in upper case). Accordingly, a GluB-1 promoter of this invention can contain a mutant form of SEQ ID NO: 3, which has one or more of SEQ ID NOs: 10, 11, and 14. Examples of such a promoter include the following sequences:

can introduce into a plant cell the promoter sequence and the recombinant nucleic acid, and cultivate the cell to generate a plant.

Finally, the invention features a method of expressing a polypeptide in a cell. The method includes (1) introducing into a host cell a recombinant nucleic acid encoding a polypeptide, wherein the recombinant nucleic acid is operatively linked to a GluB-1 promoter sequence described

```
                                                           (SEQ ID NO: 4)
GM1:
-92atatattgtctgtacgtgcaacaaactatatcaccatgTATCCATATCCActttttattgctat-28
          SEQ ID NO: 13                   SEQ ID NO: 10

(SEQ ID NO: 5)
GM2:
-92atatattgtctgtacgtgcaacaaactatatcacccctTATCCATATCCAcgcctttattgctat-28
          SEQ ID NO: 13                   SEQ ID NO: 11

(SEQ ID NO: 6)
GM3:
-92atatattgtccctacgtggcacaaactatatcacccctTATCCATATCCAcgcctttattgctat-28
          SEQ ID NO: 14                   SEQ ID NO: 11
```

Also within the scope of this invention are mutant forms of SEQ ID NO: 1 that contains SEQ ID NOs: 4-6 (i.e., SEQ ID NO: 15-17, respectively) and mutant forms of SEQ ID NO: 2 that contains SEQ ID NOs: 4-6 (i.e., SEQ ID NO: 18-20, respectively).

Each of the above-described nucleic acid sequences can be included in a promoter to drive the expression of a heterologous gene in a plant cell or transgenic plant. Thus, above, (2) culturing the host cell under conditions permitting expression of the polypeptide, and (3) recovering the polypeptide. The host cell can be cultured in the presence or absence of sugar to regulate the expression level of the polypeptide.

The details of one or more embodiments of the invention are set forth in the accompanying description below. Other advantages, features, and objects of the invention will be apparent from the detailed description and the claims.

DETAILED DESCRIPTION

The present invention relates to native GluB-1 promoter sequences, as well as their variant sequences. These sequences and variants can be used in generating plant cells or transgenic plants for producing recombinant protein.

Accordingly, the invention includes a transformed plant cell or transgenic plant containing a recombinant nucleic acid that encodes a heterologous protein. Expression of the protein is under the control of one of the GluB-1 promoter sequences described above. The plant cell can be a dicot plant cell or a monocot plant cell.

A transformed plant cell of the invention can be produced by introducing into a plant cell a vector containing a GluB-1 promoter sequence that is operatively linked to a recombinant nucleic acid encoding a desired heterologous protein. Techniques for transforming a wide variety of plant cells are well known in the art and described in the technical and scientific literature. See, for example, Weising et al., 1988, Ann. Rev. Genet. 22:421-477. To express a heterologous protein in a plant cell, the gene can be linked to a GluB-1 promoter sequence, as well as other transcriptional and translational initiation regulatory sequences that will direct the transcription of the gene and translation of the encoded protein in the plant cell.

For example, for over-expression, a constitutive plant promoter may be employed in addition to a GluB-1 promoter. A "constitutive" promoter is active under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumafaciens*, the ACT11 and Cat3 promoters from *Arabidopsis* (Huang et al., 1996, Plant Mol. Biol. 33:125-139 and Zhong et al., 1996, Mol. Gen. Genet. 251:196-203), the stearoyl-acyl carrier protein desaturase gene promoter from *Brassica napus* (Solocombe et al., 1994, Plant Physiol. 104:1167-1176), the GPc1 and Gpc2 promoters from maize (Martinez et al., 1989, J. Mol. Biol. 208:551-565 and Manjunath et al., 1997, Plant Mol. Biol. 33:97-112).

Alternatively, a plant promoter may be employed to direct expression of the heterologous gene in a specific cell type (i.e., tissue-specific promoters) or under more precise environmental or developmental control (i.e., inducible promoters). Examples of environmental conditions that may affect transcription by inducible promoters include anaerobic conditions, elevated temperature, the presence of light, spray with chemicals or hormones, or infection of a pathogen. Examples of such promoters include the root-specific ANR1 promoter (Zhang and Forde, 1998, Science 279:407) and the photosynthetic organ-specific RBCS promoter (Khoudi et al., 1997, Gene 197:343).

For proper polypeptide expression, a polyadenylation region at the 3'-end of the coding region should be included. The polyadenylation region can be derived from the natural gene, from a variety of other plant genes, or from T-DNA.

A marker gene can also be included to confer a selectable phenotype on plant cells. For example, the marker gene may encode a protein that confers biocide resistance, antibiotic resistance (e.g., resistance to kanamycin, G418, bleomycin, hygromycin), or herbicide resistance (e.g., resistance to chlorosulfuron or Basta).

A recombinant nucleic acid that encodes a heterologous protein may be introduced into the genome of a desired plant host cell by a variety of conventional techniques. For example, the recombinant nucleic acid may be introduced directly into the genomic DNA of a plant cell using techniques such as protoplast electroporation and microinjectionl, or the recombinant nucleic acid can be introduced directly to plant tissue using ballistic methods, such as DNA particle bombardment. A transformed plant cell of the invention can be produced by introducing into a plant cell a vector containing a GluB-1 promoter sequence that is operatively linked to a recombinant nucleic acid encoding a desired heterologous protein. Microinjection techniques are well documented in the scientific and patent literature. Introduction of a recombinant nucleic acid using polyethylene glycol precipitation is described in Paszkowski et al., 1984, EMBO J. 3:2717-2722. Electroporation techniques are described in Fromm et al., 1985, Proc. Natl. Acad. Sci. USA 82:5824. Ballistic transformation techniques are described in Klein et al., 1987, Nature 327:70-73.

Alternatively, the recombinant nucleic acid may be combined with suitable T-DNA flanking regions and introduced into a conventional *Agrobacterium tumefaciens* host vector. The virulence functions of the *Agrobacterium tumefaciens* host will direct the insertion of the heterologous gene and adjacent marker into the plant cell DNA when the cell is infected by the bacteria. *Agrobacterium tumefaciens*-mediated transformation techniques, including disarming and use of binary vectors, are well known in the art. See, e.g., Horsch et al., 1984, Science 233:496-498, Fraley et al., 1983, Proc. Natl. Acad. Sci. USA 80:4803, and Gene Transfer to Plants, Potrykus, ed., Springer-Verlag, Berlin, 1995.

The presence and copy number of the gene encoding a desired heterologous protein in a transgenic plant can be determined using methods well known in the art, e.g., Southern blotting analysis. Expression of the heterologous gene in a transgenic plant may be confirmed by detecting the corresponding heterologous mRNA or protein in the transgenic plant by methods well known in the art.

Transformed plant cells that are prepared by any of the above-described transformation techniques can be cultured to regenerate a whole plant. Such regeneration techniques rely on manipulation of certain phytohormones in a tissue culture growth medium, typically relying on a biocide or herbicide marker that has been introduced together with the heterologous gene. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., 1987, Ann. Rev. Plant Phys. 38:467-486. Once the heterologous gene has been confirmed to be stably incorporated in the genome of a transgenic plant, it can be introduced into other plants by sexual crossing. One or more standard breeding techniques can be used, depending upon the species to be crossed.

The above-described plant cell/plant can be either dicot or monocot. There are advantages for using a cereal plant as a host for recombinant proteins. Cereal crops (e.g., rice, corn and wheat) are grown worldwide. Further, there are well-established agricultural practices for their production, distribution and processing. They can be transported and distributed over long distances at ambient temperatures and have a long shelf life (Stoger et al., 2002, Curr Opin Biotechnol 13: 161-166; and Streatfield et al., Vaccine 19: 2742-2748). They have high annual yields and are therefore suitable for producing a large amount of protein. Unlike green tissues (e.g., tobacco and alfalfa), they have (1) lower levels of toxic secondary metabolites and (2) lower hydrolytic profiles and lower level of proteins and lipids, thereby facilitating protein purification and enhancing protein stability, respectively (Delaney, 2002, In: Plants as Factories for Protein Production Hood, E. E. and Howard, J. A., eds, Netherlands: Kluwer Academic, pp. 139-158). Recombinant proteins produced in cereals are stable during storage, due to very low water contents. Rice is one of the most important crops and staple foods in the world. As a protein expression system, rice has several advantages over other cereal crops (e.g., wheat, barley and rye), including efficient transformation technology, availability of a variety of constitutive and regulated promoters, greater biomass (yield per unit area), and lower production costs (Stoger et al., 2002, Curr. Opin. Biotechnol. 13: 161-166). Additionally, since rice is a self-pollinated crop, gene flow between wild type and transgenic species through cross-pollination is much limited. In other words, genetic contamination is minimized.

When using rice seeds as a platform for producing recombinant proteins, it is important to use promoters that control gene expression in developing rice seeds. Glutelin is the most abundant seed storage protein in rice, consisting 60%-80% of total endosperm proteins in mature seeds (Wen et al., 1985, Plant Physiol 78: 172-177; and Li et al., 1993, Plant Cell Physiol. 34: 385-390). The rice glutelin is encoded by a family of approximately 10 genes per haploid rice genome (Okita et al., 1989, J. Biol. Chem. 264: 12573-12581; and Takaiwa et al., 1991, Jpn. J. Genet. 66: 161-171). Based on the sequence similarity, rice glutelin genes could be categorized into two subfamilies, designated as GluA and GluB. Each of the GluA and GluB subfamilies contains at least four genes, with coding regions sharing 75%-95% homology. Several glutelin gene promoters have been demonstrated to be specifically active in developing rice endosperms (Wu et al., 2000, Plant J 23: 415-421; Wu et al., 1998, Plant Cell Physiol 39: 885-889; and Wu et al., 1998, Plant J 14: 673-683). The GluB promoter possesses higher activity than the GluA promoter and its cis-acting elements have been analyzed. A 245-bp region in the GluB promoter is necessary for conferring endosperm-specific expression in developing rice seeds (Yoshihara et al., 1996, Plant Cell Physiol 37: 107-111; Yoshihara et al., 1996, FEBS Lett. 383: 213-218). This region contains two AACA motifs (AACAAAC), one GCN4 motif (TGAGTCA), and one G-box. The GCN4 motif is a determinant for endosperm-specific expression, while the AACA motif and G box are responsible for quantitative regulation of the promoter.

Expressing proteins in rice seeds requires a strong, developing rice seed-specific promoter. Although several glutelin promoters have been used for expressing recombinant proteins in transgenic rice and barley seeds, the yields of these proteins are generally too low (ranging from less than 0.1% to 1% of total soluble protein) for practical use (Goto et al., 1999, Nat. Biotechnol. 17: 282-286).

Various strategies can be employed to increase promoter activity. One of them is to modify cis-acting elements in the promoter. It has been shown that the sugar response sequence (SRS) in the promoter of a rice α-amylase gene, αAmy3, functions as a transcriptional enhancer for both homologous and heterologous promoters in transient expression and stable transformation assays (Lu et al., 1998, J. Biol. Chem. 273: 10120-10131; and Chen et al., 2002, J. Biol. Chem. 277: 13641-13649). According to U.S. Pat. No. 5,460,952, rice α-amylase gene promoters are sugar-down-regulated and can be used to express recombinant protein in plant cells after the cells have been subjected to sugar starvation.

The sugar starvation-inducible expression system can be used for production of regulatory proteins. When production of recombinant protein in large quantity becomes detrimental to cell growth, this system is particularly advantageous. Cells can be grown in a regular medium containing sucrose, and little or no recombinant protein is produced. The cells can then be subjected to sucrose starvation for a short period of time to induce expression of recombinant proteins, and the growth can be resumed by switching into a sucrose-containing medium. On the hand, it is desired to produce proteins from cells cultured in the presence sucrose since it is tedious to switch between sucrose-containing and sucrose-lacking culture medium. The invention provides such an expression system that can be up-regulated by sugar, e.g., sucrose.

As indicated in the examples below, both the rice α-amylase gene promoters and glutelin gene promoters lead to high level expression of recombinant protein (up to 12% of total proteins) in media lacking and containing sucrose, respectively. Note that these two types of promoters have similar levels of efficiency. If the overexpression of the protein affects cell growth, the α-amylase gene promoter can be used. Otherwise, both types of promoters can be used. Cell growth and protein yield can then be compared and evaluated to select a more efficient and appropriate system.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

EXAMPLE 1

A GluB-1 promoter containing SEQ ID NO: 1 was used to generate transformed rice cells and transgenic rice.

Plant Material

The rice variety used in this example was *Oryza sativa L.* cv. Tainung 67. Immature seeds were dehulled, sterilized with 2.4% NaOCl for 1 hour, washed extensively with sterile water, and placed on an N6D agar medium for callus induction according to the method described in Toki, 1997, Plant Mol. Biol. Rep. 15, 16-21. After one month, callus derived from scutella were subcultured in a fresh N6D medium for transformation, or in a liquid MS medium (Murashige et al., 1962, Physiol. Plant 15:473-497) containing 3% sucrose and 10 µM 2,4-D for establishing a suspension cell culture in the manner described in Yu et al., 1991, J. Biol. Chem. 266:21131-21137.

Plasmid Construction

A 1351-bp glutelin gene promoter (shown below, nt 1-1351) was PCR-amplified using rice genomic DNA as a template. The forward primer and reverse primer were B1-5 (5'-GGG<u>GAATTC</u> GATCTCGATTTTTGAGGAAT-3' (SEQ ID NO:12), EcoRI site underlined) and B1-sp (5' GGG <u>GGATCC</u> GGGATTAAATAGCTGGGCCA-3' (SEQ ID NO:21), BamHI site underlined), respectively. A 75-bp sequence encoding a putative signal peptide (sp) sequence is also shown below (nt 1352-1426). The putative 25-amino acid signal peptide cleavage site was predicted based on a statistical method (von Heijne, 1985, J. Mol. Biol. 184, 99-105).

(SEQ ID NO:7)

```
   1 GATCTCGATT TTTGAGGAAT TTTAGAAGTT GAACAGAGTC AATCGAACAG ACAGTTGAAG
  61 AGATATGGAT TTTCTAAGAT TAATTGATTC TCTGTCTAAA GAAAAAAGT ATTATTGAAT
 121 TAAATGGAAA AAGAAAAAGG AAAAAGGGGA TGGCTTCTGC TTTTTGGGCT GAAGGCGGCG
 181 TGTGGCCAGC GTGCTGCGTG CGGACAGCGA GCGAACACAC GACGGAGCAG CTACGACGAA
 241 CGGGGGACCG AGTGGACCGG ACGAGGATGT GGCCTAGGAC GAGTGCACAA GGCTAGTGGA
 301 CTCGGTCCCC GCGCGGTATC CCGAGTGGTC CACTGTCTGC AAACACGATT CACATAGAGC
 361 GGGCAGAGGC GGGAGCCGTC CTAGGTGCAC CGGAAGCAAA TCCGTCGCCT GGGTGGATTT
 421 GAGTGACACG GCCCACGTGT AGCCTCACAG CTCTCCGTGG TCAGATGTGT AAAATTATCA
 481 TAATATGTGT TTTTCAAATA GTTAAATAAT ATATATAGGC AAGTTATATG GGTCAATAAG
 541 CAGTAAAAAG GCTTATGACA TGGTAAAATT ACTTACACCA ATATGCCTTA CTGTCTGATA
 601 TATTTTACAT GACAACAAAG TTACAAGTAC GTCATTTAAA AATACAAGTT ACTTATCAAT
 661 TGTAGTGTAT CAAGTAAATG ACAACAAACC TACAAATTTG CTATTTTGAA GGAACACTTA
 721 AAAAAATCAA TAGGCAAGTT ATATAGTCAA TAAACTGCAA GAAGGCTTAT GACATGGAAA
 781 AATTACATAC ACCAATATGC TTTATTGTCC GGTATATTTT ACAAGACAAC AAAGTTATAA
 841 GTATGTCATT TAAAAATACA AGTTACTTAT CAATTGTCAA GTAAATGAAA ACAAACCTAC
 901 AAATTTGTTA TTTTGAAGGA ACACCTAAAT TATCAAATAT AGCTTGGTAC GCAAAATGAC
 961 AACATGCTTA CAAGTTATTA TCATCTTAAA GTTAGAGTCA TCTTCTCAAG CATAAGAGCT
1021 TTATGGTGCA AAAACAAATA TAATGACAAG GCAAAGATAC ATACATATTA AGAGTATGGA
1081 CAGACATTTC TTTAACAAAC TCCATTTGTA TTACTCCAAA AGCACCAGAA GTTTGTCATG
1141 GCTGAGTCAT GAAATGTATA GTTCAATCTT GCAAAGTTGC CTTTCCTTTT GTACTGTGTT
1201 TTAACACTAC AAGCCATATA TTGTCTGTAC GTGCAACAAA CTATATCACC ATGTATCCGA
1261 AGATGCTTTT TTATTGCTAT ATAAACTAGC TTGGTCTGTC TTTGAACTCA CATCAATTAG
1321 CTTAAGTTTC CATAAGCAAG TACAAATAGC TATGGCGAGT TCCGTTTTCT CTCGGTTTTC
1381 TATATACTTT TGTGTTCTTC TATTATGCCA TGGTTCTATG GCCCAGCTAT TAATCCC
```

The PCR-amplified GluB-1 promoter-signal peptide sequence was digested with EcoRI and BamHI and subcloned into the corresponding sites in pBluescript (Strategene) to generate pBS-G and pBS-Gp. The promoter sequence was then placed upstream of the coding region of Apu to make translational fusion constructs.

A sequence encoding a truncated Apu amino acid 75 to 1029 was PCR-amplified using genomic DNA of T. ethanolicus 39E as a template (Mathupala et al., 1993, J. Biol. Chem. 268:16332-16344). The forward primer and reverse primer were 5'-CG<u>GGATTCC</u>TTAAGCTTGCATCTTGA-3' (SEO ID NO:22) (BamHI site underlined) and 5'-CCG<u>GCGGCCGC</u>CTACATATTTTCCCCTTGGCCA-3' (SEQ ID NO:23) (NotI site underlined), respectively. The PCR product was digested with BamHI and NotI and fused downstream of the GluB-1 promoter-signal peptide sequence in pBS-Gp to make translational fusion to generate pBS-Gp-Apu.

The nopaline synthase gene germinator (Nos 3') was PCR-amplified using pBI221 (Clontech) as the DNA template. The forward and reverse primers were 5'-TCC<u>GAGCTC</u>CAGATCGTTCAAACATTT-3' (SEQ ID NO:24) (Sad site underlined) and 5'-AGC<u>GAGCTC</u>GATCGATCTAGTAACAT-3' (SEQ ID NO:25') (Sad underlined), respectively. The Nos 3'UTR was digested with SacI and fused downstream of Apu in pBS-Gp-Apu to generate pBS-Gp-Apu-Nos.

A 1.2 kb aAmy8 promoter-signal peptide sequence was excised with SalI and HindIII from pAG8 (Chan et al., 1993, Plant Mol. Biol. 22:491-506.) and subcloned into pBluescript to generate pBS/8sp. The aAmy8 3'UTRs were PCR-amplified from a RAMYG6a plasmid (Yu et al., 1992, Gene 122: 247-253) using 5'-CG<u>CCGCGG</u> TAGCTTTAGCTAT-AGCGAT-3' (SEQ ID NO:26) (SacII site underlined, forward primer) and 5'-TCC<u>CCGCGGG</u>TCCTCTAAGTGAACCGT-3' (SEQ ID NO: 27) (SacII underlined, reverse primer). RAMYG6a contains the 3'half coding sequence and 3' flanking region of aAmy8 genomic DNA and was generated by the screening of a rice genomic DNA library (Clontech) using aAmy8-C as a probe. The aAmy8 3'UTRs were subcloned into the SacII sites of pBS/8sp to generate pBS/8sp8U. The truncated apu was cut with BamHI and NotI and subcloned into the same sites in pBS-8sp8U to generate pBS-aAmy8-sp-Apu-8U.

A 1.1-kb sequence containing an αAmy3 promoter-signal peptide sequence was excised with SalI and HindIII from p3G-13211 (Lu et al., 1998, J. Biol. Chem. 273, 10120-10131.) and subcloned into pBluescript to generate pBS-3sp. The αAmy3 3'UTR was excised with HindIII and SacI from pMTC37 (Chan and Yu, 1998, Plant J. 15:685-696.)

and subcloned into the corresponding sites in pBS-3sp to generate pBS-3sp3U. The above-described truncated apu sequence was digested with BamHI and NotI and subcloned into the same sites in pBS-3sp3U to generate pBS-αAmy3-sp-Apu-3U.

DNA sequencing was conducted and confirmed that the above-described ligations were correct or in-frame. Then, the GluB-sp-Apu-Nos, αAmy3-sp-Apu-αAmy3 3'UTR, and αAmy8-sp-Apu-αAmy8 3'UTR chimeric genes were excised from pBS-Gp-Apu-Nos, pBS-αAmy3-sp-Apu-3U, and pBS-αAmy8-sp-Apu-8U with SalI, blunt-ended, and inserted into the HindIII-digested and blunt-ended binary vector pSMY1H (Ho et al., 2000, Plant Physiol. 122, 57-66) to generate pGpApu, pA3Apu and pA8Apu, respectively.

Transgenic Rice

The above-described plasmids pGpApu, pA3Apu, and pA8Apu, were respectively introduced into *Agrobacterium tumefaciens* strain EHA101 (Hood et al., 1986, J. Bacteriol. 168,1291-1301) with an electroporator (BTX) according to the manufacturer's instruction and delivered to the rice genome. Calli induced from immature rice seeds were transformed with *Agrobacterium* according to the methods described by Hiei et al., 1994, Plant J. 6:271-282; and Toki, 1997, Plant Mol. Biol. Rep. 15, 16-21. Transformed rice calli were then selected on a medium containing hygromycin.

Identity of the transformed rice cells was confirmed with genomic DNA Southern blot analysis. More specifically, rice seeds were germinated and grown in the dark for 1 week. Genomic DNA was isolated from the wild type or transformed calli according to the method described in Sheu et al., 1996, J Biol. Chem. 271:26998-27004. Ten μg of genomic DNA was digested with restriction enzymes, fractionated in 0.8% agarose gel, and transferred to a nylon membrane (MSI). Hybridization was performed at 42° C. using a $^{32}$P random primer labeled APU cDNA probe.

Expression of APU in *E. coli* and Preparation of Polyclonal Antibodies

APU was expressed in *E. coli*. More specifically, the sequence encoding Apu amino acids 75 to 1029 was PCR-amplified from genornic DNA of T. ethanolicus 39E (ATCC53033), which was prepared according to the method of Sheu et al. just mentioned. Primers used were 5'-CG CATATGTTAAGCTTGCATCTTG- ATTC-3' (SEQ ID NO:28') (forward primer, NdeI site underlined) and 5'-CCG CTCGAGCTACATATTTTC- CCCTTGGCCA-3' (SEQ ID NO:29) (reverse primer, XhoI site underlined). The amplified DNA fragment was digested with NdeI and XhoI and ligated into the same sites in pET20b(+) (Novagen) to generate pET-APU. After introducing pET-APU into *E. coli* strain BL21 (DE3), APU protein was expressed and purified according to the instruction provided by Novagen. The *E. coli* expressed APU has extra 6 histidines and 25 amino acid residues at C terminal, which increase the molecular weight of APU by about 3.4 kD. One hundred mg of purified APU were injected into a New Zealand White rabbit at 4-6 week interval to generate polyclonal antibodies according to the methods described in Williams et al., 1995, In: DNA Cloning 2. Expression Systems. A Practical approach. (Ed) Glover D M and Hames B D. IRL Press, New York.).

APU Expression in Transformed Rice Suspension Cells is Sugar-regulated

The above-described transformed rice calli were cultured in a liquid MS medium to generate a suspension cell culture. Culture media of cells expressing APU fused with signal peptides were collected and analyzed by both Enzyme-linked immunosorbent assay (ELISA) and protein gel blot analyses according to the methods described in Ausubel et al. 1992, Short Protocols in Molecular Biology. 2$^{nd}$ edit. In: A Compendium of Methods from Current Protocols in Molecular Biology. John Wiley & Sons. New York.).

In the ELISA, the *E. coli*-expressed APU was used as a standard. The percentage APU in total medial proteins was then obtained. The total protein concentration was determined using a Bio-Rad protein assay kit based on the dye-binding assay of Bradford (Bradford, 1976, Anal Biochem 72:248-254.). In the protein gel blot analysis, total proteins were extracted from cultured suspension cells with an extraction buffer (50 mM Tris-HCl, pH 8.8, 1 mM EDTA, 10% glycerol, 1% Triton X-100, 10 mM β-mercaptoethanol, and 0.1% sarkosyl). The culture medium was collected and centrifuged at 18,000 g at 4° C. for 15 min to remove cell debris. Western blot analysis was performed as described in Yu et al., 1991, J. Biol. Chem. 266:21131-21137.

The results show that relatively high level expressions of APU were found in media of transformed suspension cells and no APU was detected in media of non-transformed cells. The levels of APU varied from line to line, possibly due to a position effect or multiple copy gene effect on transgene expression. The presence of APU in the culture media indicates that the putative signal sequence of GluB-1 is capable of directing translocation of APU through the secretary pathway. The αAmy3 and αAmy8 promoters directed higher levels of APU expression in the absence of sucrose than in the presence of sucrose. This result was expected as activity of αAmy3 and αAmy8 promoters is up-regulated by sucrose starvation (Lu et al., 1998, J. Biol. Chem. 273, 10120-10131). Interestingly, the GluB-1 promoter directed a higher level of APU expression in rice suspension cells in the presence of sucrose than in the absence of sucrose, suggesting that the activity of the GluB-1 promoter is up regulated by sucrose in cultured rice suspension cells.

The molecular weight of APU expressed by the transformed rice cells is similar as that expressed by *E. Coli*, indicating that the APU expressed by rice cells are approximately 3.4 kD larger than the theoretic molecular weight. Since APU has three potential glycosylation sites, this result suggests that glycosylation of APU has occurred in rice cells.

Further analysis indicated that high expression levels APU were obtained under the control of an a-amylase promoter (in the absence of sucrose) and the above-described glutelin promoter (in the presence of sucrose). The highest levels were up to 12% of total proteins, which are much higher than those of the *E.coli* repression system described above. This result suggests that these two promoters have similar efficiency in directing expression of recombinant proteins in cultured suspension cells.

EXAMPLE 2

GluB-1 promoters containing SEQ ID NO: 9 or 14 were used to generate transformed rice cells and transgenic rice. The rice variety used in this example was the s *Oryza sativa* L. cv. Tainung 67. Immature seeds were dehulled, sterilized with 2.4% NaOCl for 1 hour, washed extensively with sterile water, and placed on CIM agar medium (Toki, 1997, Plant Mol. Biol. Rep. 15, 16-21) for callus induction. After one month, calli derived from scutella were subcultured in a fresh CIM medium for transformation.

Plasmid Construction

The 1351-bp rice GluB-1 promoter described above in Example 1 was PCR-amplified and subcloned into pBluescript to generate pBS/GluB-1, which was subsequently used as a template for all PCR-based mutagenesis. Modification of the GluB-1 promoter was carried out by a two-step PCR sequence substitution method, using P1 and P2 as primers in the primary PCR for generating a megaprimer P3 and then using P3 and P4 primers in the secondary PCR for generating modified promoter regions. The P2 (5'-CGC GATATCGTACTTGCTTATGG-3', (SEQ ID NO:30) EcoRV site underlined) and P4 (5'-GTCATGGCTGAG TCATGAAATG-3'(SEQ ID NO:31) BspHI site underlined) primers were used in PCR for each modified GluB-1 promoter.

For construction of a GM 1 promoter, in which the TA box-like (TATCCC) sequence in the GluB-1 promoter was substituted by two tandemly repeated TA boxes, P1(GM1) primer (5'-ATATATTGTCTGTACGTGCAACAAAC-TATATCACCATG TATCCATATCCAAAGATGCTTTTTTATTGCTAT-3' (SEQ ID NO:32), tandemly repeated TA box underlined) and P2 primer were used for amplification of fragment M1. For construction of a GM2 promoter, in which sequences flanking the tandemly repeated TA box in the GM1 promoter were substituted with sequences flanking TA box in SRS, P1 (GM2) primer (5'-ATATATTGTCTGTACGTGCAA-CAAACTATATCACCcctTATCCATA TCCACgccTTTATTGCTAT-3' (SEQ ID NO:33, TA box underlined and modified flanking sequences in bold lowercase) and P2 primer were used for amplification of fragment M2. For construction of a GM3 promoter, in which sequences flanking the G-box in the GM2 promoter were substituted with sequences flanking the G box in SRS, P1(GM3) primer (5'-ATATATTGTCcc TACGTGgcACAAACTATATCACCcct TATCCATATCCAC gccTTTATTGCTAT-3' (SEQ ID NO:34), G box and TA box underlined and modified flanking sequences in bold lowercase) and P2 primer were used for amplification of fragment M3. DNA fragment between the BspHI and EcoRV sites in the GluB-1 promoter was substituted by fragment M1, M2, or M3 to generate pBS/GM1, pBS/GM2, and pBS/GM3, respectively.

To fuse the *luciferase* (Luc) gene downstream of the wild type or modified GluB-1 promoter, a Luc-Nos 3' fragment was isolated from pJD312 (Luehrsen et al., Methods Enzymol. 216: 397-414) with SalI and Bgl II and inserted into the SalI and BamHI sites of pBS to generate pBS/LN. The Luc-Nos3' fragment was then excised from pBS/LN by SalI and XbaI, end-blunted, and inserted into the EcoRV site in pBS/GluB-1, pBS/GM 1, pBS/GM2, and pBS/GM3 to generate pBS/GLN, pBS/GM1LN, pBS/GM2LN, and pBS/GM3LN, respectively.

A sequence was excised with EcoRI from pTRA151 (Zheng et al., 1991, Plant Physiol. 97: 832-835). This sequence contained a cauliflower mosaic virus 35S RNA (CaMV35S) promoter-hygromycin B phosphotransferase (Hpt) coding sequence-tumor morphology large gene 3'UTR (tml) fusion gene. It was then subcloned into the EcoRI site of the binary vector pPZP200 (Hajdukiewicz et al., 1994, Plant Mol. Biol. 25: 989-994) to generate pPZP/HPH. pPZP/HPH was then linearized with KpnI and served as a vector backbone. pBS/GLN, pBS/GM1LN, pBS/GM2LN, and pBS/GM3LN were linearized with KpnI and respectively inserted into this vector backbone to generate pGLN, pGM1LN, pGM2LN, and pGM3LN, respectively.

Transgenic Rice

The just-described pGLN, pGM1LN, pGM2LN, and pGM3LN were introduced into rice using *Agrobacterium tumefaciens* strain EHA101 in the same manner described above in Example 1. Each of the resultant transgenic lines was then examined for the copy number of transgene in its genome by DNA gel blot analysis. More specifically, genomic DNA was isolated from rice leaves according to the method described in Sheu et al., 1996, J. Biol. Chem. 271:26998-27004. Ten µg genomic DNA was digested with SpeI, separated in a 0.7% agarose gel, and transferred to a nylon membrane (MSI). The membrane was then hybridized with a 2 kb $^{32}$P-labeled Luc-Nos 3'DNA fragment probe. It was found that each of the transgenic lines had about 1-5 copies of the transgene, except that GLN-2 seemed to have more than 5 copies.

Suspension Cell Culture and Promoter Analysis

Calli were prepared from the just-described transgenic rice plants using standard techniques and were selected for bhygromycin resistance to establish suspension cells. The cells were cultured on a reciprocal shaker at 120 rpm and incubated at 26° C. in dark. They were subcultured every 7 days by transferring 0.5 mL of the cell culture into 25 mL of fresh liquid MS medium in a 125-mL flask. To examine the regulation effects of sugar, sucrose was added to the callus culture (in a CIM ) or suspension cell culture (in an MS liquid medium) to reach a final concentration of 3%. After an incubation of 24 hours at 28° C. in the dark, 0.5 g callus or suspension cell culture were collected for promoter analysis.

More specifically, total proteins were extracted from calli, cultured suspension cells, or matured rice grains using a CCLR buffer (100 mM $KH_2PO_4$, pH 7.8, 1 mM EDTA, 10% glycerol, 1% Triton X-100, 7 mM β-mercaptoethanol). Protein concentrations were determined using a Coomassie protein assay reagent (Bio-Rad). The activity of each GluB-1 promoter was examined using luciferase activity assay according to the method described in Lu et al., 1998, J. Biol. Chem. 273: 10120-10131.

It was found that, in all three types of cells, the above-described three modified promoters (GM1, GM2, and GM3) exhibited stronger promoter activity than the promoter having the above-described 1351 bp region (GluB-1) in either absence or presence of sucrose. In general, promoter activities were higher in the absence of sucrose than in the presence of sucrose. Based on their promoter activities, the promoters were ranked from the strongest to the weakest. The ranking is shown in Table 1 below:

TABLE 1

| Cell Type | Promoter strength ranking |
|---|---|
| | Promoter Strength |
| Rice calli | GM3 > GM2 > GM1 > GluB-1 |
| Rice suspension cells | |
| in presence of sucrose | GM3 > GM2 > GM1 > GluB-1 |
| in absence of sucrose | GM3 > GM1 > GM2 > GluB-1 |
| Rice seeds | GM3 > GM2 > GM1 > GluB-1 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A nucleic acid comprising a mutant rice glutelin GluB-1 promoter or its full-length complement, said promoter being selected from the group consisting of:
   (a) SEQ ID NO:17,
   (b) SEQ ID NO:20, and
   (c) a fragment of SEQ ID NO:17 or SEQ ID NO:20 having promoter activity, wherein said fragment contains a seguence having both SEQ ID NOs:14 and 9; and said nucleic acid exhibits stronger promoter activity than the wild-type rice-glutelin GluB-1 promoter.

2. The nucleic acid of claim 1, wherein the GluB-1 promoter contains SEQ ID NO:6, or the full-length complement thereof.

3. The nucleic acid of claim 2, wherein the GluB-1 promoter contains SEQ ID NO: 17 or 20, or the full-length complement thereof.

4. A vector comprising the nucleic acid of claim 1.

5. A transformed plant cell comprising
   a promoter sequence that contains the nucleic acid of claim 1; and
   a recombinant nucleic acid that encodes a heterologous protein,
   wherein the promoter sequence is operatively linked to the recombinant nucleic acid.

6. The plant cell of claim 5, wherein the plant cell is a monocot plant cell.

7. The plant cell of claim 6, wherein the plant cell is a cereal plant cell.

8. The plant cell of claim 7, wherein the plant cell is a rice cell, a corn cell, a wheat cell, a barley cell, an oat cell, or a sorghum cell.

9. The plant cell of claim 5, wherein the plant cell is a dicot plant cell.

10. The plant cell of claim 9, wherein the plant cell is a tobacco cell, a potato cell, a tomato cell, or a soybean cell.

11. A transgenic plant comprising a genome that includes
    a promoter sequence that contains the nucleic acid of claim 1; and
    a recombinant nucleic acid that encodes a heterologous protein,
    wherein the promoter sequence is operatively linked to the recombinant nucleic acid.

12. The transgenic plant of claim 11, wherein the plant is a monocot plant.

13. The transgenic plant of claim 12, wherein the plant is a cereal plant.

14. The transgenic plant of claim 13, wherein the plant is a rice, corn, wheat, barley, oat, or sorghum plant.

15. The transgenic plant of claim 11, wherein the plant is a dicot plant.

16. The transgenic plant of claim 15, wherein the plant is a tobacco, potato, tomato, or soybean plant.

17. A method of producing a transformed plant cell, the method comprising introducing into a plant cell a promoter sequence that contains the nucleic acid of claim 1; and a recombinant nucleic acid that encodes a heterologous protein, wherein the promoter sequence is operatively linked to the recombinant nucleic acid.

18. A method of producing a transgenic plant, the method comprising:
    introducing into a plant cell a promoter sequence that contains the nucleic acid of claim 1; and a recombinant nucleic acid that encodes a heterologous protein, wherein the promoter sequence is operatively linked to the recombinant nucleic acid; and
    cultivating the cell to generate a plant.

19. A method of expressing a polypeptide in a cell, the method comprising
    introducing into a host cell a recombinant nucleic acid encoding a polypeptide, wherein the recombinant nucleic acid is operatively linked to the nucleic acid of claim 1; and
    culturing the host cell under conditions permitting expression of the polypeptide.

20. The method of claim 19, wherein the host cell is cultured in the presence or absence of sugar.

21. The method of claim 19, further comprising recovering the polypeptide.

22. The nucleic acid of claim 1, wherein the GluB-1 promoter, once operatively linked to a nucleic acid that encodes a polypeptide, directs the expression of the polypeptide in suspension cells of a plant in the presence of sucrose.

* * * * *

SEQUENCE LISTING

<160> NUMBER OF SEQ ID NOS: 34

<210> SEQ ID NO 1
<211> LENGTH: 1306
<212> TYPE: DNA
<213> ORGANISM: Oryza sativa

<400> SEQUENCE: 1

```
gatctcgatt tttgaggaat tttagaagtt gaacagagtc aatcgaacag acagttgaag      60
agatatggat tttctaagat taattgattc tctgtctaaa gaaaaaaagt attattgaat     120
taaatggaaa aagaaaaagg aaaaagggga tggcttctgc tttttgggct gaaggcggcg     180
tgtggccagc gtgctgcgtg cggacagcga gcgaacacac gacggagcag ctacgacgaa     240
cgggggaccg agtggaccgg acgaggatgt ggcctaggac gagtgcacaa ggctagtgga     300
ctcggtcccc gcgcggtatc ccgagtggtc cactgtctgc aaacacgatt cacatagagc     360
gggcagacgc gggagccgtc ctaggtgcac cggaagcaaa tccgtcgcct gggtggattt     420
gagtgacacg gcccacgtgt agcctcacag ctctccgtgg tcagatgtgt aaaattatca     480
taatatgtgt ttttcaaata gttaaataat atatataggc aagttatatg ggtcaataag     540
cagtaaaaag gcttatgaca tggtaaaatt acttacacca atatgcctta ctgtctgata     600
tattttacat gacaacaaag ttacaagtac gtcatttaaa aatacaagtt acttatcaat     660
tgtagtgtat caagtaaatg acaacaaacc tacaaatttg ctattttgaa ggaacactta     720
aaaaaatcaa taggcaagtt atatagtcaa taaactgcaa gaaggcttat gacatggaaa     780
aattacatac accaatatgc tttattgtcc ggtatatttt acaagacaac aaagttataa     840
gtatgtcatt taaaaataca agttacttat caattgtcaa gtaaatgaaa acaaacctac     900
aaatttgtta ttttgaagga cacctaaat tatcaaatat agcttgctac gcaaaatgac     960
aacatgctta caagttatta tcatcttaaa gttagactca tcttctcaag cataagagct    1020
ttatggtgca aaaacaaata taatgacaag gcaaagatac atacatatta agagtatgga    1080
cagacatttc tttaacaaac tccatttgta ttactccaaa agcaccagaa gtttgtcatg    1140
gctgagtcat gaaatgtata gttcaatctt gcaaagttgc cttccttttt gtactgtgtt    1200
ttaacactac aagccatata ttgtctgtac gtgcaacaaa ctatatcacc atgtatccca    1260
agatgctttt ttattgctat ataaactagc ttggtctgtc tttgaa                   1306
```

<210> SEQ ID NO 2
<211> LENGTH: 1343
<212> TYPE: DNA
<213> ORGANISM: Oryza sativa

<400> SEQUENCE: 2

```
gatctcgatt tttgaggaat tttagaagtt gaacagagtc aatcgaacag acagttgaag      60
agatatggat tttctaagat taattgattc tctgtctaaa gaaaaaaagt attattgaat     120
taaatggaaa aagaaaaagg aaaaagggga tggcttctgc tttttgggct gaaggcggcg     180
tgtggccagc gtgctgcgtg cggacagcga gcgaacacac gacggagcag ctacgacgaa     240
cgggggaccg agtggaccgg acgaggatgt ggcctaggac gagtgcacaa ggctagtgga     300
ctcggtcccc gcgcggtatc ccgagtggtc cactgtctgc aaacacgatt cacatagagc     360
gggcagacgc gggagccgtc ctaggtgcac cggaagcaaa tccgtcgcct gggtggattt     420
gagtgacacg gcccacgtgt agcctcacag ctctccgtgg tcagatgtgt aaaattatca     480
```

```
taatatgtgt ttttcaaata gttaaataat atatataggc aagttatatg ggtcaataag       540
cagtaaaaag gcttatgaca tggtaaaatt acttacacca atatgcctta ctgtctgata       600
tattttacat gacaacaaag ttacaagtac gtcatttaaa aatacaagtt acttatcaat       660
tgtagtgtat caagtaaatg acaacaaacc tacaaatttg ctattttgaa ggaacactta       720
aaaaaatcaa taggcaagtt atatagtcaa taaactgcaa gaaggcttat gacatggaaa       780
aattacatac accaatatgc tttattgtcc ggtatatttt acaagacaac aaagttataa       840
gtatgtcatt taaaaataca agttacttat caattgtcaa gtaaatgaaa acaaacctac       900
aaatttgtta ttttgaagga cacctaaat tatcaaatat agcttgctac gcaaaatgac        960
aacatgctta caagttatta tcatcttaaa gttagactca tcttctcaag cataagagct       1020
ttatggtgca aaaacaaata taatgacaag gcaaagatac atacatatta agagtatgga      1080
cagacatttc tttaacaaac tccatttgta ttactccaaa agcaccagaa gtttgtcatg       1140
gctgagtcat gaaatgtata gttcaatctt gcaaagttgc ctttcctttt gtactgtgtt       1200
ttaacactac aagccatata ttgtctgtac gtgcaacaaa ctatatcacc atgtatccca       1260
agatgctttt ttattgctat ataaactagc ttggtctgtc tttgaactca catcaattag       1320
cttaagtttc cataagcaag tac                                              1343

<210> SEQ ID NO 3
<211> LENGTH: 65
<212> TYPE: DNA
<213> ORGANISM: Artificial Sequence
<220> FEATURE:
<223> OTHER INFORMATION: Mutantation from Oryza sativa

<400> SEQUENCE: 3
atatattgtc tgtacgtgca acaaactata tcaccatgta tcccaagatg ctttttttatt      60 gctat                                                                  65

<210> SEQ ID NO 4
<211> LENGTH: 65
<212> TYPE: DNA
<213> ORGANISM: Artificial Sequence
<220> FEATURE:
<223> OTHER INFORMATION: Mutantation from Oryza sativa

<400> SEQUENCE: 4
atatattgtc tgtacgtgca acaaactata tcaccatgta tccatatcca cttttttatt      60
gctat                                                                  65

<210> SEQ ID NO 5
<211> LENGTH: 65
<212> TYPE: DNA
<213> ORGANISM: Artificial Sequence
<220> FEATURE:
<223> OTHER INFORMATION: Mutantation from Oryza sativa

<400> SEQUENCE: 5
atatattgtc tgtacgtgca acaaactata tcaccccta tccatatcca cgcctttatt        60
gctat                                                                  65

<210> SEQ ID NO 6
<211> LENGTH: 65
<212> TYPE: DNA
<213> ORGANISM: Artificial Sequence
<220> FEATURE:
```

<223> OTHER INFORMATION: Mutantation from Oryza sativa

<400> SEQUENCE: 6

```
atatattgtc cctacgtggc acaaactata tcaccccctta tccatatcca cgcctttatt    60
gctat                                                                 65
```

<210> SEQ ID NO 7
<211> LENGTH: 1438
<212> TYPE: DNA
<213> ORGANISM: Oryza sativa

<400> SEQUENCE: 7

```
gatctcgatt tttgaggaat tttagaagtt gaacagagtc aatcgaacag acagttgaag     60
agatatggat tttctaagat taattgattc tctgtctaaa gaaaaaaagt attattgaat    120
taaatggaaa agaaaaaagg aaaaagggga tggcttctgc ttttttgggct gaaggcggcg   180
tgtggccagc gtgctgcgtg cggacagcga gcgaacacac gacggagcag ctacgacgaa   240
cgggggaccg agtggaccgg acgaggatgt ggcctaggac gagtgcacaa ggctagtgga   300
ctcggtcccc gcgcggtatc ccgagtggtc cactgtctgc aaacacgatt cacatagagc   360
gggcagacgc gggagccgtc ctaggtgcac cggaagcaaa tccgtcgcct gggtggattt   420
gagtgacacg gcccacgtgt agcctcacag ctctccgtgg tcagatgtgt aaaattatca   480
taatatgtgt ttttcaaata gttaaataat atatataggc aagttatatg ggtcaataag   540
cagtaaaaag gcttatgaca tggtaaaatt acttacacca atatgcctta ctgtctgata   600
tattttacat gacaacaaag ttacaagtac gtcatttaaa aatacaagtt acttatcaat   660
tgtagtgtat caagtaaatg acaacaaacc tacaaatttg ctattttgaa ggaacactta   720
aaaaaatcaa taggcaagtt atatagtcaa taaactgcaa gaaggcttat gacatggaaa   780
aattacatac accaatatgc tttattgtcc ggtatatttt acaagacaac aaagttataa   840
gtatgtcatt taaaaataca agttacttat caattgtcaa gtaaatgaaa acaaacctac   900
aaatttgtta ttttgaagga cacctaaat tatcaaatat agcttgctac gcaaaatgac   960
aacatgctta caagttatta tcatcttaaa gttagactca tcttctcaag cataagagct  1020
ttatggtgca aaaacaaata taatgacaag gcaaagatac atacatatta agagtatgga  1080
cagacatttc tttaacaaac tccatttgta ttactccaaa agcaccagaa gtttgtcatg  1140
gctgagtcat gaaatgtata gttcaatctt gcaaagttgc ctttccttt gtactgtgtt   1200
ttaacactac aagccatata ttgtctgtac gtgcaacaaa ctatatcacc atgtatccca  1260
agatgctttt ttattgctat ataaactagc ttggtctgtc tttgaactca catcaattag  1320
cttaagtttc cataagcaag tacaaatagc tatggcgagt tccgtttct ctcggttttc   1380
tatatacttt tgtgttcttc tattatgcca tggttctatg gcccagctat taatccc      1438
```

<210> SEQ ID NO 8
<211> LENGTH: 12
<212> TYPE: DNA
<213> ORGANISM: Artificial Sequence
<220> FEATURE:
<223> OTHER INFORMATION: Mutantation from Oryza sativa

<400> SEQUENCE: 8

```
tatcccaaga tg                                                         12
```

<210> SEQ ID NO 9
<211> LENGTH: 12

```
<212> TYPE: DNA
<213> ORGANISM: Artificial Sequence
<220> FEATURE:
<223> OTHER INFORMATION: Mutantation from Oryza sativa

<400> SEQUENCE: 9
tatccatatc ca                                                        12

<210> SEQ ID NO 10
<211> LENGTH: 19
<212> TYPE: DNA
<213> ORGANISM: Artificial Sequence
<220> FEATURE:
<223> OTHER INFORMATION: Mutantation from Oryza sativa

<400> SEQUENCE: 10
atgtatccat atccactttt                                                19

<210> SEQ ID NO 11
<211> LENGTH: 19
<212> TYPE: DNA
<213> ORGANISM: Artificial Sequence
<220> FEATURE:
<223> OTHER INFORMATION: Mutantation from Oryza sativa

<400> SEQUENCE: 11
ccttatccat atccacgcc                                                 19

<210> SEQ ID NO 12
<211> LENGTH: 29
<212> TYPE: DNA
<213> ORGANISM: Artificial Sequence
<220> FEATURE:
<223> OTHER INFORMATION: Primer

<400> SEQUENCE: 12
ggggaattcg atctcgattt ttgaggaat                                      29

<210> SEQ ID NO 13
<211> LENGTH: 10
<212> TYPE: DNA
<213> ORGANISM: Artificial Sequence
<220> FEATURE:
<223> OTHER INFORMATION: Mutantation from Oryza sativa

<400> SEQUENCE: 13
tgtacgtgca                                                           10

<210> SEQ ID NO 14
<211> LENGTH: 10
<212> TYPE: DNA
<213> ORGANISM: Artificial Sequence
<220> FEATURE:
<223> OTHER INFORMATION: Mutantation from Oryza sativa

<400> SEQUENCE: 14
cctacgtggc                                                           10

<210> SEQ ID NO 15
<211> LENGTH: 1306
<212> TYPE: DNA
<213> ORGANISM: Artificial Sequence
<220> FEATURE:
<223> OTHER INFORMATION: Mutantation from Oryza sativa

<400> SEQUENCE: 15
```

| | |
|---|---|
| gatctcgatt tttgaggaat tttagaagtt gaacagagtc aatcgaacag acagttgaag | 60 |
| agatatggat tttctaagat taattgattc tctgtctaaa gaaaaaaagt attattgaat | 120 |
| taaatgaaaa agaaaaagg aaaaagggga tggcttctgc ttttttgggct gaaggcggcg | 180 |
| tgtggccagc gtgctgcgtg cggacagcga gcgaacacac gacggagcag ctacgacgaa | 240 |
| cgggggaccg agtggaccgg acgaggatgt ggcctaggac gagtgcacaa ggctagtgga | 300 |
| ctcggtcccc gcgcggtatc ccgagtggtc cactgtctgc aaacacgatt cacatagagc | 360 |
| gggcagacgc gggagccgtc ctaggtgcac cggaagcaaa tccgtcgcct gggtggattt | 420 |
| gagtgacacg gcccacgtgt agcctcacag ctctccgtgg tcagatgtgt aaaattatca | 480 |
| taatatgtgt ttttcaaata gttaaataat atatataggc aagttatatg ggtcaataag | 540 |
| cagtaaaaag gctatgaca tggtaaaatt acttacacca atatgcctta ctgtctgata | 600 |
| tattttacat gacaacaaag ttacaagtac gtcatttaaa aatacaagtt acttatcaat | 660 |
| tgtagtgtat caagtaaatg acaacaaacc tacaaatttg ctattttgaa ggaacactta | 720 |
| aaaaaatcaa taggcaagtt atatagtcaa taaactgcaa gaaggcttat gacatggaaa | 780 |
| aattacatac accaatatgc tttattgtcc ggtatatttt acaagacaac aaagttataa | 840 |
| gtatgtcatt taaaaataca agttacttat caattgtcaa gtaaatgaaa acaaacctac | 900 |
| aaatttgtta ttttgaagga cacctaaat tatcaaatat agcttgctac gcaaaatgac | 960 |
| aacatgctta caagttatta tcatcttaaa gttagactca tcttctcaag cataagagct | 1020 |
| ttatggtgca aaaacaaata taatgacaag gcaaagatac atacatatta agagtatgga | 1080 |
| cagacatttc tttaacaaac tccatttgta ttactccaaa agcaccagaa gtttgtcatg | 1140 |
| gctgagtcat gaaatgtata gttcaatctt gcaaagttgc ctttcctttt gtactgtgtt | 1200 |
| ttaacactac aagccatata ttgtctgtac gtgcaacaaa ctatatcacc atgtatccat | 1260 |
| atccactttt ttattgctat ataaactagc ttggtctgtc tttgaa | 1306 |

<210> SEQ ID NO 16
<211> LENGTH: 1306
<212> TYPE: DNA
<213> ORGANISM: Artificial Sequence
<220> FEATURE:
<223> OTHER INFORMATION: Mutantation from Oryza sativa

<400> SEQUENCE: 16

| | |
|---|---|
| gatctcgatt tttgaggaat tttagaagtt gaacagagtc aatcgaacag acagttgaag | 60 |
| agatatggat tttctaagat taattgattc tctgtctaaa gaaaaaaagt attattgaat | 120 |
| taaatgaaaa agaaaaagg aaaaagggga tggcttctgc ttttttgggct gaaggcggcg | 180 |
| tgtggccagc gtgctgcgtg cggacagcga gcgaacacac gacggagcag ctacgacgaa | 240 |
| cgggggaccg agtggaccgg acgaggatgt ggcctaggac gagtgcacaa ggctagtgga | 300 |
| ctcggtcccc gcgcggtatc ccgagtggtc cactgtctgc aaacacgatt cacatagagc | 360 |
| gggcagacgc gggagccgtc ctaggtgcac cggaagcaaa tccgtcgcct gggtggattt | 420 |
| gagtgacacg gcccacgtgt agcctcacag ctctccgtgg tcagatgtgt aaaattatca | 480 |
| taatatgtgt ttttcaaata gttaaataat atatataggc aagttatatg ggtcaataag | 540 |
| cagtaaaaag gctatgaca tggtaaaatt acttacacca atatgcctta ctgtctgata | 600 |
| tattttacat gacaacaaag ttacaagtac gtcatttaaa aatacaagtt acttatcaat | 660 |
| tgtagtgtat caagtaaatg acaacaaacc tacaaatttg ctattttgaa ggaacactta | 720 |
| aaaaaatcaa taggcaagtt atatagtcaa taaactgcaa gaaggcttat gacatggaaa | 780 |

```
aattacatac accaatatgc tttattgtcc ggtatatttt acaagacaac aaagttataa      840
gtatgtcatt taaaaataca agttacttat caattgtcaa gtaaatgaaa acaaacctac      900
aaatttgtta ttttgaagga acacctaaat tatcaaatat agcttgctac gcaaaatgac      960
aacatgctta caagttatta tcatcttaaa gttagactca tcttctcaag cataagagct     1020
ttatggtgca aaaacaaata taatgacaag gcaaagatac atacatatta agagtatgga     1080
cagacatttc tttaacaaac tccatttgta ttactccaaa agcaccagaa gtttgtcatg     1140
gctgagtcat gaaatgtata gttcaatctt gcaaagttgc cttcctttt gtactgtgtt      1200 ttaacactac aagccatata ttgtctgtac gtgcaacaaa ctatatcacc ccttatccat     1260
atccacgcct ttattgctat ataaactagc ttggtctgtc tttgaa                    1306
```

<210> SEQ ID NO 17  
<211> LENGTH: 1306  
<212> TYPE: DNA  
<213> ORGANISM: Artificial Sequence  
<220> FEATURE:  
<223> OTHER INFORMATION: Mutantation from Oryza sativa

<400> SEQUENCE: 17

```
gatctcgatt tttgaggaat tttagaagtt gaacagagtc aatcgaacag acagttgaag       60
agatatggat tttctaagat taattgattc tctgtctaaa gaaaaaaagt attattgaat      120
taaatggaaa aagaaaaagg aaaaaggggga tggcttctgc tttttgggct gaaggcggcg     180
tgtggccagc gtgctgcgtg cggacagcga gcgaacacac gacggagcag ctacgacgaa     240
cgggggaccg agtggaccgg acgaggatgt ggcctaggac gagtgcacaa ggctagtgga     300
ctcggtcccc gcgcggtatc ccgagtggtc cactgtctgc aaacacgatt cacatagagc     360
gggcagacgc gggagccgtc ctaggtgcac cggaagcaaa tccgtcgcct gggtggattt     420
gagtgacacg gcccacgtgt agcctcacag ctctccgtgg tcagatgtgt aaaattatca     480
taatatgtgt ttttcaaata gttaaataat atatataggc aagttatatg ggtcaataag     540
cagtaaaaag gcttatgaca tggtaaaatt acttacacca atatgcctta ctgtctgata     600
tattttacat gacaacaaag ttacaagtac gtcatttaaa aatacaagtt acttatcaat     660
tgtagtgtat caagtaaatg acaacaaacc tacaaatttg ctattttgaa ggaacactta     720
aaaaaatcaa taggcaagtt atatagtcaa taaactgcaa gaaggcttat gacatggaaa     780
aattacatac accaatatgc tttattgtcc ggtatatttt acaagacaac aaagttataa     840
gtatgtcatt taaaaataca agttacttat caattgtcaa gtaaatgaaa acaaacctac     900
aaatttgtta ttttgaagga acacctaaat tatcaaatat agcttgctac gcaaaatgac     960
aacatgctta caagttatta tcatcttaaa gttagactca tcttctcaag cataagagct    1020
ttatggtgca aaaacaaata taatgacaag gcaaagatac atacatatta agagtatgga    1080
cagacatttc tttaacaaac tccatttgta ttactccaaa agcaccagaa gtttgtcatg    1140
gctgagtcat gaaatgtata gttcaatctt gcaaagttgc cttcctttt gtactgtgtt     1200 ttaacactac aagccatata ttgtccctac gtggcacaaa ctatatcacc ccttatccat    1260
atccacgcct ttattgctat ataaactagc ttggtctgtc tttgaa                   1306
```

<210> SEQ ID NO 18  
<211> LENGTH: 1343  
<212> TYPE: DNA  
<213> ORGANISM: Artificial Sequence  
<220> FEATURE:

<223> OTHER INFORMATION: Mutantation from Oryza sativa

<400> SEQUENCE: 18

```
gatctcgatt tttgaggaat tttagaagtt gaacagagtc aatcgaacag acagttgaag    60
agatatggat tttctaagat taattgattc tctgtctaaa gaaaaaagt attattgaat    120
taaatgaaaa aagaaaaagg aaaaagggga tggcttctgc tttttgggct gaaggcggcg    180
tgtggccagc gtgctgcgtg cggacagcga gcgaacacac gacggagcag ctacgacgaa    240
cgggggaccg agtggaccgg acgaggatgt ggcctaggac gagtgcacaa ggctagtgga    300
ctcggtcccc gcgcggtatc ccgagtggtc cactgtctgc aaacacgatt cacatagagc    360
gggcagacgc gggagccgtc ctaggtgcac cggaagcaaa tccgtcgcct gggtggattt    420
gagtgacacg gcccacgtgt agcctcacag ctctccgtgg tcagatgtgt aaaattatca    480
taatatgtgt ttttcaaata gttaaataat atatataggc aagttatatg ggtcaataag    540
cagtaaaaag gctattgaca tggtaaaatt acttacacca atatgcctta ctgtctgata    600
tattttacat gacaacaaag ttacaagtac gtcatttaaa aatacaagtt acttatcaat    660
tgtagtgtat caagtaaatg acaacaaacc tacaaatttg ctattttgaa ggaacactta    720
aaaaaatcaa taggcaagtt atatagtcaa taaactgcaa gaaggcttat gacatggaaa    780
aattacatac accaatatgc tttattgtcc ggtatatttt acaagacaac aaagttataa    840
gtatgtcatt taaaaataca agttacttat caattgtcaa gtaaatgaaa acaaacctac    900
aaatttgtta ttttgaagga cacctaaat tatcaaatat agcttgctac gcaaaatgac    960
aacatgctta caagttatta tcatcttaaa gttagactca tcttctcaag cataagagct   1020
ttatggtgca aaaacaaata taatgacaag gcaaagatac atacatatta agagtatgga   1080
cagacatttc tttaacaaac tccatttgta ttactccaaa agcaccagaa gtttgtcatg   1140
gctgagtcat gaaatgtata gttcaatctt gcaaagttgc ctttccttttt gtactgtgtt   1200
ttaacactac aagccatata ttgtctgtac gtgcaacaaa ctatatcacc atgtatccat   1260
atccactttt ttattgctat ataaactagc ttggtctgtc tttgaactca catcaattag   1320
cttaagtttc cataagcaag tac                                           1343
```

<210> SEQ ID NO 19
<211> LENGTH: 1343
<212> TYPE: DNA
<213> ORGANISM: Artificial Sequence
<220> FEATURE:
<223> OTHER INFORMATION: Mutantation from Oryza sativa

<400> SEQUENCE: 19

```
gatctcgatt tttgaggaat tttagaagtt gaacagagtc aatcgaacag acagttgaag    60
agatatggat tttctaagat taattgattc tctgtctaaa gaaaaaagt attattgaat    120
taaatgaaaa aagaaaaagg aaaaagggga tggcttctgc tttttgggct gaaggcggcg    180
tgtggccagc gtgctgcgtg cggacagcga gcgaacacac gacggagcag ctacgacgaa    240
cgggggaccg agtggaccgg acgaggatgt ggcctaggac gagtgcacaa ggctagtgga    300
ctcggtcccc gcgcggtatc ccgagtggtc cactgtctgc aaacacgatt cacatagagc    360
gggcagacgc gggagccgtc ctaggtgcac cggaagcaaa tccgtcgcct gggtggattt    420
gagtgacacg gcccacgtgt agcctcacag ctctccgtgg tcagatgtgt aaaattatca    480
taatatgtgt ttttcaaata gttaaataat atatataggc aagttatatg ggtcaataag    540
cagtaaaaag gctattgaca tggtaaaatt acttacacca atatgcctta ctgtctgata    600
```

-continued

```
tattttacat gacaacaaag ttacaagtac gtcatttaaa aatacaagtt acttatcaat      660
tgtagtgtat caagtaaatg acaacaaacc tacaaatttg ctattttgaa ggaacactta      720
aaaaaatcaa taggcaagtt atatagtcaa taaactgcaa gaaggcttat gacatggaaa      780
aattacatac accaatatgc tttattgtcc ggtatatttt acaagacaac aaagttataa      840
gtatgtcatt taaaaataca agttacttat caattgtcaa gtaaatgaaa acaaacctac      900
aaatttgtta ttttgaagga cacctaaat tatcaaatat agcttgctac gcaaaatgac      960
aacatgctta caagttatta tcatcttaaa gttagactca tcttctcaag cataagagct     1020
ttatggtgca aaaacaaata taatgacaag gcaaagatac atacatatta agagtatgga     1080
cagacatttc tttaacaaac tccatttgta ttactccaaa agcaccagaa gtttgtcatg     1140
gctgagtcat gaaatgtata gttcaatctt gcaaagttgc ctttcctttt gtactgtgtt     1200
ttaacactac aagccatata ttgtctgtac gtgcaacaaa ctatatcacc ccttatccat     1260
atccacgcct ttattgctat ataaactagc ttggtctgtc tttgaactca catcaattag     1320
cttaagtttc cataagcaag tac                                             1343
```

<210> SEQ ID NO 20
<211> LENGTH: 1343
<212> TYPE: DNA
<213> ORGANISM: Artificial Sequence
<220> FEATURE:
<223> OTHER INFORMATION: Mutantation from Oryza sativa

<400> SEQUENCE: 20

```
gatctcgatt tttgaggaat tttagaagtt gaacagagtc aatcgaacag acagttgaag       60
agatatggat tttctaagat taattgattc tctgtctaaa gaaaaaagt attattgaat      120
taaatggaaa agaaaaagg aaaagggga tggcttctgc ttttgggct gaaggcggcg        180
tgtggccagc gtgctgcgtg cggacagcga gcgaacacac gacggagcag ctacgacgaa     240
cgggggaccg agtggaccgg acgaggatgt ggcctaggac gagtgcacaa ggctagtgga     300
ctcggtcccc gcgcggtatc ccgagtggtc cactgtctgc aaacacgatt cacatagagc     360
gggcagacgc gggagccgtc ctaggtgcac cggaagcaaa tccgtcgcct gggtggattt     420
gagtgacacg gccacgtgt agcctcacag ctctccgtgg tcagatgtgt aaaattatca     480
taatatgtgt ttttcaaata gttaaataat atatataggc aagttatatg ggtcaataag     540
cagtaaaaag gcttatgaca tggtaaaatt acttacacca atatgcctta ctgtctgata     600
tattttacat gacaacaaag ttacaagtac gtcatttaaa aatacaagtt acttatcaat     660
tgtagtgtat caagtaaatg acaacaaacc tacaaatttg ctattttgaa ggaacactta     720
aaaaaatcaa taggcaagtt atatagtcaa taaactgcaa gaaggcttat gacatggaaa     780
aattacatac accaatatgc tttattgtcc ggtatatttt acaagacaac aaagttataa     840
gtatgtcatt taaaaataca agttacttat caattgtcaa gtaaatgaaa acaaacctac     900
aaatttgtta ttttgaagga cacctaaat tatcaaatat agcttgctac gcaaaatgac     960
aacatgctta caagttatta tcatcttaaa gttagactca tcttctcaag cataagagct    1020
ttatggtgca aaaacaaata taatgacaag gcaaagatac atacatatta agagtatgga    1080
cagacatttc tttaacaaac tccatttgta ttactccaaa agcaccagaa gtttgtcatg    1140
gctgagtcat gaaatgtata gttcaatctt gcaaagttgc ctttcctttt gtactgtgtt    1200
ttaacactac aagccatata ttgtccctac gtggcacaaa ctatatcacc ccttatccat    1260
```

```
atccacgcct ttattgctat ataaactagc ttggtctgtc tttgaactca catcaattag    1320
cttaagtttc cataagcaag tac                                            1343
```

<210> SEQ ID NO 21
<211> LENGTH: 29
<212> TYPE: DNA
<213> ORGANISM: Artificial Sequence
<220> FEATURE:
<223> OTHER INFORMATION: Primer

<400> SEQUENCE: 21

```
gggggatccg ggattaaata gctgggcca                                        29
```

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22

```
cgggattcct taagcttgca tcttga                                           26
```

<210> SEQ ID NO 23
<211> LENGTH: 33
<212> TYPE: DNA
<213> ORGANISM: Artificial Sequence
<220> FEATURE:
<223> OTHER INFORMATION: Primer

<400> SEQUENCE: 23

```
ccggcggccg cctacatatt ttccccttgg cca                                   33
```

<210> SEQ ID NO 24
<211> LENGTH: 27
<212> TYPE: DNA
<213> ORGANISM: Artificial Sequence
<220> FEATURE:
<223> OTHER INFORMATION: Primer

<400> SEQUENCE: 24

```
tccgagctcc agatcgttca aacattt                                          27
```

<210> SEQ ID NO 25
<211> LENGTH: 26
<212> TYPE: DNA
<213> ORGANISM: Artificial Sequence
<220> FEATURE:
<223> OTHER INFORMATION: Primer

<400> SEQUENCE: 25

```
agcgagctcg atcgatctag taacat                                           26
```

<210> SEQ ID NO 26
<211> LENGTH: 27
<212> TYPE: DNA
<213> ORGANISM: Artificial Sequence
<220> FEATURE:
<223> OTHER INFORMATION: Primer

<400> SEQUENCE: 26

```
cgccgcggta gctttagcta tagcgat                                          27
```

<210> SEQ ID NO 27
<211> LENGTH: 27

```
<212> TYPE: DNA
<213> ORGANISM: Artificial Sequence
<220> FEATURE:
<223> OTHER INFORMATION: Primer

<400> SEQUENCE: 27
tccccgcggg tcctctaagt gaaccgt                                          27

<210> SEQ ID NO 28
<211> LENGTH: 28
<212> TYPE: DNA
<213> ORGANISM: Artificial Sequence
<220> FEATURE:
<223> OTHER INFORMATION: Primer

<400> SEQUENCE: 28
cgcatatgtt aagcttgcat cttgattc                                         28

<210> SEQ ID NO 29
<211> LENGTH: 31
<212> TYPE: DNA
<213> ORGANISM: Artificial Sequence
<220> FEATURE:
<223> OTHER INFORMATION: Primer

<400> SEQUENCE: 29
ccgctcgagc tacatatttt ccccttggcc a                                     31

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
cgcgatatcg tacttgctta tgg                                              23

<210> SEQ ID NO 31
<211> LENGTH: 22
<212> TYPE: DNA
<213> ORGANISM: Artificial Sequence
<220> FEATURE:
<223> OTHER INFORMATION: Primer

<400> SEQUENCE: 31
gtcatggctg agtcatgaaa tg                                               22

<210> SEQ ID NO 32
<211> LENGTH: 71
<212> TYPE: DNA
<213> ORGANISM: Artificial Sequence
<220> FEATURE:
<223> OTHER INFORMATION: Primer

<400> SEQUENCE: 32
atatattgtc tgtacgtgca acaaactata tcaccatgta tccatatcca aagatgcttt      60
tttattgcta t                                                           71

<210> SEQ ID NO 33
<211> LENGTH: 65
<212> TYPE: DNA
<213> ORGANISM: Artificial Sequence
<220> FEATURE:
<223> OTHER INFORMATION: Primer
```

-continued

```
<400> SEQUENCE: 33
atatattgtc tgtacgtgca acaaactata tcaccccta tccatatcca cgcctttatt    60
gctat                                                               65

<210> SEQ ID NO 34
<211> LENGTH: 65
<212> TYPE: DNA
<213> ORGANISM: Artificial Sequence
<220> FEATURE:
<223> OTHER INFORMATION: Primer

<400> SEQUENCE: 34
atatattgtc cctacgtggc acaaactata tcaccccta tccatatcca cgcctttatt    60
gctat                                                               65
```